(12) United States Patent
Karimov et al.

(10) Patent No.: US 10,391,285 B2
(45) Date of Patent: Aug. 27, 2019

(54) MOTION-ASSISTED SYSTEMS, DEVICES AND METHODS FOR MINIMIZING OBSTRUCTION OF MEDICAL DEVICES

(71) Applicant: THE CLEVELAND CLINIC FOUNDATION, Cleveland, OH (US)

(72) Inventors: Jamshid Karimov, Cleveland Hts., OH (US); Kiyotaka Fukamachi, Mayfield Hts., OH (US); Ray Dessoffy, Parma, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 443 days.

(21) Appl. No.: 14/301,770

(22) Filed: Jun. 11, 2014

(65) Prior Publication Data
US 2014/0371725 A1    Dec. 18, 2014

Related U.S. Application Data

(60) Provisional application No. 61/835,065, filed on Jun. 14, 2013.

(51) Int. Cl.
*A61M 27/00* (2006.01)
*A61M 25/01* (2006.01)
*A61M 25/00* (2006.01)
*A61B 90/70* (2016.01)

(52) U.S. Cl.
CPC ....... *A61M 27/00* (2013.01); *A61B 2090/701* (2016.02); *A61M 2025/0019* (2013.01)

(58) Field of Classification Search
CPC ................. A61M 27/00; A61M 25/01; A61M 2202/0014; A61M 2202/0492; A61M 2205/10; A61M 2210/1039; A61M 2025/0019; A61M 2039/167; A61M 2210/10; A61M 2210/101; A61M 2210/1014; A61M 2210/1017; A61M 2210/1021; A61F 9/00754; A61B 5/0051; A61B 2017/22011; A61B 2017/22005; A61B 17/22004; A61B 17/22012; A61B 2017/22014; A61B 2017/22015
See application file for complete search history.

(56) References Cited

U.S. PATENT DOCUMENTS

| | | | | |
|---|---|---|---|---|
| 3,159,384 A | * | 12/1964 | Davis | B01F 11/0014 211/74 |
| 3,850,580 A | * | 11/1974 | Moore | B01F 11/0014 366/277 |
| 4,509,947 A | | 4/1985 | Lattin | |
| 4,555,183 A | * | 11/1985 | Thomas | B01F 11/0014 200/332 |
| 4,698,058 A | | 10/1987 | Greenfeld et al. | |
| 4,883,644 A | * | 11/1989 | Perlman | B01L 9/06 366/110 |
| 4,906,238 A | * | 3/1990 | Greenfeld | A61M 25/0017 604/22 |

(Continued)

*Primary Examiner* — Adam Marcetich
(74) *Attorney, Agent, or Firm* — Tarolli, Sundheim, Covell & Tummino LLP

(57) ABSTRACT

Systems, devices and methods for minimizing or preventing catheter or other medical device occlusion. Mechanical motion is applied to the inner and outer walls of the catheter to minimize blood clots or other biological substances from obstructing the catheter and to help maintain catheter patency.

19 Claims, 4 Drawing Sheets

(56) References Cited

U.S. PATENT DOCUMENTS

| | | | | |
|---|---|---|---|---|
| 4,932,935 | A * | 6/1990 | Swartz | A61B 17/32002 604/22 |
| 5,243,997 | A * | 9/1993 | Uflacker | A61B 17/22012 600/585 |
| 5,380,273 | A * | 1/1995 | Dubrul | A61B 17/22 601/3 |
| 5,399,013 | A * | 3/1995 | Sawyer | B01F 11/0028 366/110 |
| 5,443,078 | A * | 8/1995 | Uflacker | A61B 17/22012 600/585 |
| 5,449,369 | A * | 9/1995 | Imran | A61B 17/2202 600/585 |
| 5,524,635 | A * | 6/1996 | Uflacker | A61B 17/22012 600/585 |
| 5,549,119 | A * | 8/1996 | Solar | A61B 17/22012 600/585 |
| 6,852,097 | B1 | 2/2005 | Fulton, III | |
| 6,936,025 | B1 * | 8/2005 | Evans | A61B 17/22 604/22 |
| 7,892,191 | B2 | 2/2011 | Zumeris et al. | |
| 2002/0055689 | A1 * | 5/2002 | Kaplan | A61B 10/0233 600/567 |
| 2004/0199228 | A1 * | 10/2004 | Wilson | A61B 8/546 607/101 |
| 2005/0038376 | A1 * | 2/2005 | Zumeris | A61L 2/02 604/22 |
| 2006/0161098 | A1 * | 7/2006 | Nita | A61B 17/22012 604/22 |
| 2006/0253154 | A1 * | 11/2006 | Equils | A61J 17/02 606/235 |
| 2007/0212265 | A1 * | 9/2007 | Ebers | B01F 11/0008 422/400 |
| 2007/0244423 | A1 * | 10/2007 | Zumeris | A61M 25/0017 604/22 |
| 2008/0097465 | A1 * | 4/2008 | Rollins | A61M 25/09041 606/108 |
| 2008/0103419 | A1 * | 5/2008 | Adamson | A61H 7/007 601/84 |
| 2008/0208083 | A1 * | 8/2008 | Lin | A61M 27/008 601/2 |
| 2009/0188531 | A1 * | 7/2009 | Boyle, Jr. | A61B 19/34 134/22.11 |
| 2009/0264833 | A1 * | 10/2009 | Boyle, Jr. | B08B 9/0436 604/257 |
| 2010/0233021 | A1 * | 9/2010 | Sliwa | A61M 25/0017 422/20 |
| 2013/0338544 | A1 * | 12/2013 | Newell | A61N 7/02 601/2 |

* cited by examiner

MOTION-ASSISTED SYSTEMS, DEVICES AND METHODS FOR MINIMIZING OBSTRUCTION OF MEDICAL DEVICES

RELATED APPLICATION

This application claims priority from U.S. Provisional Application No. 61/835,065, filed 14 Jun. 2013, the subject matter of which is incorporated herein by reference in its entirety.

TECHNICAL FIELD

The present invention relates to systems, devices and methods for minimizing obstructions and maintaining patency in catheters and other medical devices having lumens or hollowed portions.

BACKGROUND

Catheters, such a chest tubes, are routinely used in patients who have had cardiothoracic surgery or chest trauma to drain blood and other biological matter. Use of chest tubes helps maintain cardiorespiratory/hemodynamic stability by avoiding complications related to accumulation of blood and thrombi (blood clots), air, debris, or other fluids in the pericardial sac and pleural space. However, chest tubes often clog after surgery and their occlusion can lead to life threatening complications such as hemothorax, acute tamponade, and pericardial effusion. This compromises postsurgical hemodynamics, adversely influences surgical outcome, and delays recovery. Chest drainage has recently been reported as an independent potential risk factor and predictor of mortality and is also associated with other adverse outcomes, including longer stays in the intensive care unit or hospital and increased duration on mechanical ventilation. Despite many improvements in intra-/post operative care, chest-tube obstruction remains an important contributor to adverse effects on patients' adequate recovery after surgery. In serious cases, the surgeon brings the patient back into the operating room to remove clots around the heart to prevent pericardial tamponade and thus cardiogenic shock. This scenario suggests that the detriment in outcomes associated with postoperative bleeding may be related to inefficient clearing of blood and retained clots from the chest due to chest-tube clogging.

The management of chest tubes has traditionally consisted of makeshift mechanical methods such as milking and tapping the external portion of the tube to remove clots and maintain patency of the tubing. One of the more controversial methods is chest tube stripping, which can generate transient high negative intrathoracic pressure and can actually be detrimental to areas being drained. Milking of chest tubes may inadvertently push any clots back into the intrathoracic portion that may occlude the tube eyelets. It has also been shown that the degree of clogging cannot always be appreciated by inspecting the tubes prior to removal because the intrathoracic portion of the chest tube may be occluded even when the extrathoracic portion appears clear. This state of uncertainty emphasizes the critical need to address current chest tube clearance strategies or to find ways by which to test chest tube clearance systems as a way to improve outcomes and possibly reduce hospital costs. Barriers to progress in the field are how to prevent clogging and maintain patency for the full length of the tube, especially the intrathoracic portion where the side and end holes collect blood that has been shed within the chest.

Currently, there is no reliable method to prevent chest-tube clogging. A heparin coating allows small amounts of molecular heparin to diffuse into the tube's lumen and also makes the tuber's inner surface slippery (low coefficient of friction), but this diffusion has a very limited time frame to maintain therapeutic efficacy. Another option is electroactive polymers embedded in the tube surface to alternately expand and contract, facilitating tube clearance. To reduce pain, drains that change from a larger diameter when placed within the body (to attain the largest drainage area possible) to a smaller diameter prior to removal have been proposed. Also, a variety of tubes with local anesthetics have been introduced to reduce the patient's discomfort and pain. Most solutions cannot provide a prolonged effect and/or cannot be controlled, safe and reliable at the same time. In addition, all existing solutions are limited in their mechanism of action to the tube's inner surface.

Therefore new and more efficient systems, devices and methods to prevent clot formation on both inner and outer surfaces of chest tubes, catheters, and other medical devices with lumens and to maintain patency of drainage tubes is necessary to reduce clot accumulation within the chest and complications linked to that condition. Further, there is a need for a chest-tube drainage system and method that reliably can be implemented without concern for clogging, not only for heart and lung surgery, but especially for expanding minimally invasive and higher acuity urgent and emergent cases.

SUMMARY

In general, the present invention provides systems, devices and methods to minimize occlusion of catheter's lumen by a substance, help maintain the catheter's patency, improve and/or enhance the functionality of the catheter, remotely or directly provide short-term or long-term effects on biological substances inside the catheter and or in the area surrounding the catheter.

In particular, the present invention provides a catheter drainage system, such as a chest tube drainage system, that applies mechanical motion to the lumen of the catheter to minimize blood clots and/or other biological substances from adhering to the catheter walls when the walls are moving. The mechanical motion applied to the catheter preferably prevent biological substances from adhering to inner walls and preferably also outer walls of the catheter to prevent clogging inside (and preferably also outside) the catheter and to maintain the patency of the catheter.

In an embodiment, the present invention provides a device comprising a body configured to attach to a catheter in an operative state. The catheter has a proximal end, a distal end, and a lumen therebetween. The body comprises a housing including a mechanical motion source electrically coupled to an electrical energy source in an operative state. The mechanical motion source is configured to deliver mechanical motion to the catheter along the lumen, preferably towards the distal end. The mechanical motion is sufficient to minimize obstruction of the catheter by a biological substance. Preferably, the mechanical motion prevents, minimizes or otherwise influences adherence of a biological substance to the inner and/or outer wall of the catheter. The mechanical motion also preferably prevents or minimizes solidification of biological fluids and their derivates. Also, preferably the mechanical motion helps maintain the catheter's patency inside and/or outside the patient's body. Further, preferably the mechanical motion helps maintain the catheter's flow characteristics.

In another embodiment, the present invention provides a system comprising a catheter and a device. The catheter has a proximal end, a distal end, and a lumen therebetween. The device comprises a body configured to couple to the catheter in an operative state. The body comprises a housing including a mechanical motion source electrically coupled to an electrical energy source in an operative state. The mechanical motion is configured to deliver mechanical motion to the catheter along the lumen, preferably towards the distal end. The mechanical motion is sufficient to minimize obstruction of the catheter by a biological substance. Preferably, the mechanical motion prevents, minimizes or otherwise influences adherence of a biological substance to the inner and/or outer wall of the catheter. The mechanical motion also preferably prevents or minimizes solidification of biological fluids and their derivates. Also, preferably the mechanical motion helps maintain the catheter's patency inside and/or outside the patient's body. Further, preferably the mechanical motion helps maintain the catheter's flow characteristics.

In another embodiment, the present invention provides a method of minimizing obstruction of a catheter having an interior portion configured to be disposed inside a patient's body, an exterior portion configured to be disposed outside of a patient's body, a proximal end, a distal end, and a lumen between the proximal and distal ends. The method comprises delivering mechanical motion to the catheter along the lumen, preferably towards the distal end. The mechanical motion is sufficient to minimize obstruction of the catheter by a biological substance. Preferably, the mechanical motion prevents, minimizes or otherwise influences adherence of a biological substance to the inner and/or outer wall of the catheter. The mechanical motion also preferably prevents or minimizes solidification of biological fluids and their derivates. Also, preferably the mechanical motion helps maintain the catheter's patency inside and/or outside the patient's body. Further, preferably the mechanical motion helps maintain the catheter's flow characteristics.

DETAILED DESCRIPTION

Figure 1:
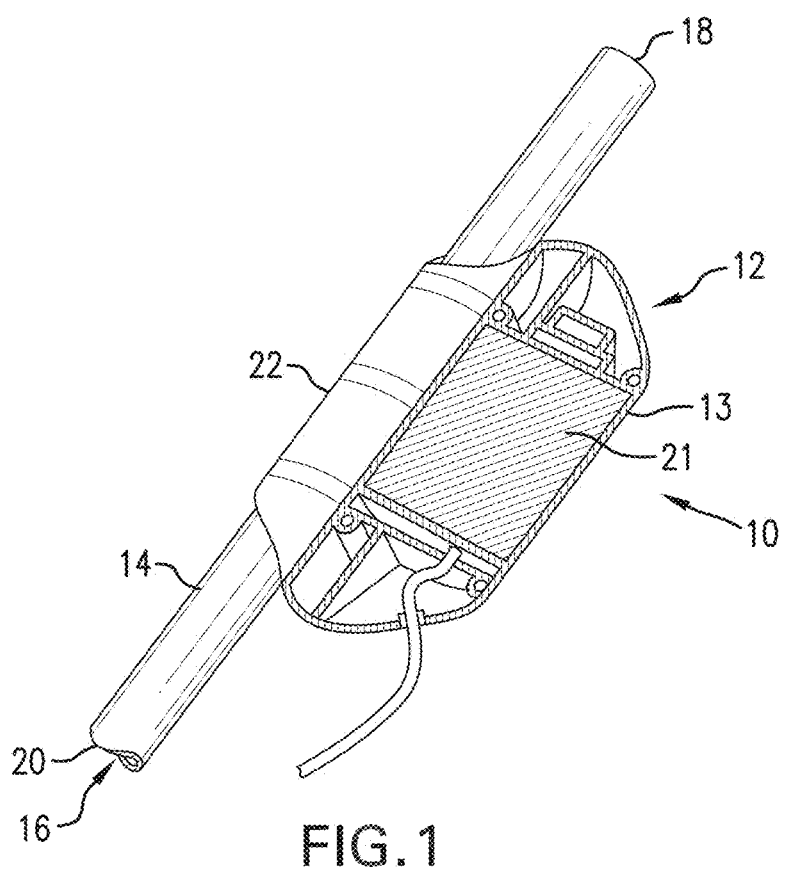
FIG. 1 is a cross-sectional view of an embodiment of a device of the present invention attached to a medical device.

Although embodiments of the present invention will be described with respect to a chest tube drain or catheter, the systems, devices and methods can apply to other types of medical device having a lumen or hollowed area that is at risk of becoming occluded and/or collapsing. Non-limiting examples of such medical devices include drainage tubes, catheters (tubular and non-tubular), fluid lines, other tubular structure, and devices with hollow bodies. Further, although embodiments of the present invention will be described with respect to a blood clot occluding a catheter, the present invention provides systems, devices and methods to minimize or prevent catheter obstruction by other fluids, including other biological fluids. In addition, although the mechanical motion delivered to the medical device will be described with respect to delivering a vibratory force, other types of mechanical motion can be applied to the medical device such as fluctuation or oscillation. Further, although a motor is mostly described as the mechanical motion source, other motion sources can be used such as an electric motor, a mechanical and/or electro-mechanical system that powers the device and/or assists, accelerates, or enhances the device with motion or any other suitable energy activated device or system. Also, electrical motion can also be applied to the medical device so long as the motion achieves the purposes as disclosed herein.

The disclosure herein refers to a patient. A patient is a mammal, including a human being. The disclosure herein also refers to an "operative state." This is the configuration of the system or device when the device is applying or is ready to apply motion to the catheter. By "integral" or "integrated" is meant that the described components are molded as one piece during manufacturing or the described components are otherwise not separable using a normal amount of force without damaging the integrity (i.e. tearing) of either component. A normal amount of force is the amount of force a user would use to remove a component meant to be separated from the other component without damaging either structure. Further, as used herein with respect to a described component, the terms "a," "an," and "the" include at least one or more of the described component, feature or element unless otherwise indicated. Moreover, the term "or" includes the term "and/or" unless otherwise indicated. In addition, it will be understood that when an element is referred to as being "on," "attached" to, "connected" to, "coupled" with, "contacting," etc., another element, it can be directly on, attached to, connected to, coupled with, or contacting the other element or intervening elements may also be present. In contrast, when an element is referred to as being, for example, "directly on," "directly attached" to, "directly connected" to, "directly coupled" with, or "directly contacting" another element, there are no intervening elements present.

In an embodiment, the present invention provides a catheter drainage system, such as a chest tube drainage system, that apply vibration to the lumen of the catheter to minimize blood clots and/or other biological substances from adhering to the catheter walls when the walls are vibrating. In a preferred embodiment, the vibration or vibratory force is applied to the entire length of the catheter's lumen. If clots cannot stick to the chest tube wall, the risk of clot buildup and tube occlusion is greatly reduced. Methods of the present invention maintain chest tube patency, which eliminates potential complications and liberates caregivers from performing repetitive inspections and manipulations at the bedside. Also, since drainage is assisted, there is no or minimal clot obstruction. As such, chest tube size may be reduced to lessen pain, improve wound healing, and provide better patient comfort postoperatively. Generally, small chest tubes are considered to be more likely to clog. However, smaller chest tubes can be as effective as large tubes in draining fluid if enhanced by vibrational motion to prevent blood clotting inside the tubes according to methods of the present invention.

Accordingly, embodiments of the present invention can reduce the complications and pain associated with obstructed chest tubes thus improving outcomes and survival. One way in which pain can be reduced is by using smaller diameter tubes. Embodiments of the present invention prevent or minimize intra-tube depositions and maintain tube patency. In addition, systems can increase short and long term performance of biomedical catheters and devices that are exposed to the blood stream (such as, for example, chest tubes, scopes, lines, other biomedical tubes, and needles), when changes in intraluminal fluid characteristics may create an obstruction.

With reference to FIG. 1, in an embodiment, device 10 comprises body 12. Body 12 comprises a housing 13 configured to couple to catheter 14 in an operative state. Only a portion of catheter 14 is illustrated in FIG. 1. Catheter 14 comprises a proximal end towards section 16, a distal end towards section 18 and a lumen 20 extending therebetween. Housing 13 comprises a mechanical motion source, such as a vibration source, electrically coupled to an electrical energy source (not shown) in an operative state. FIG. 1 illustrates the vibration source being a motor 21. The motor is configured to deliver mechanical motion, such as a vibratory force, to the catheter along lumen 20, preferably towards distal end of section 18. The mechanical motion is sufficient to minimize obstruction of catheter 14 by a biological substance, such as a blood clot. In preferred embodiments, the mechanical motion is sufficient to apply motion to the entire length of the catheter. This may prevent the initial deposit of blood and therefore subsequent clot formation. Thus, since there is no clot buildup, no obstruction can occur and the tube remains patent. Also preferably, the mechanical motion delivered by the motor is sufficient to prevent clot attachment to not only the catheter's inner surface but also the catheter's outer surface, which can improve drainage through open apertures of the catheter. This mechanical motion, such as a vibratory force, and its unique "swirling" effect on fluid inside the tube can enhance the functional characteristics of current catheters, such as chest tubes.

Regarding the power source, preferably the power source allows the user to select customized amplitudes, frequencies and/or current of the electrical energy delivered to the device. Regarding the vibration source, preferably the vibration source, such as a motor, can change the levels of vibration conveyed to the catheter thus enabling adjustability of amplitude to each given clinical condition. Further systems can include a motor with ball bearings that can be sealed and a controller. Further, the motor can have various speeds such as speeds 24 kpm or above, which will increase the vibrational frequency range, allowing the most efficacious amplitude and frequency to be utilized. To this end, the motor can also include a speed controller to maintain set constant frequencies. In another embodiment, a device includes a motor with the eccentric mass as an assembled unit. Preferably, there is a sealed interface around the motor and vibrating mass.

Figure 2:
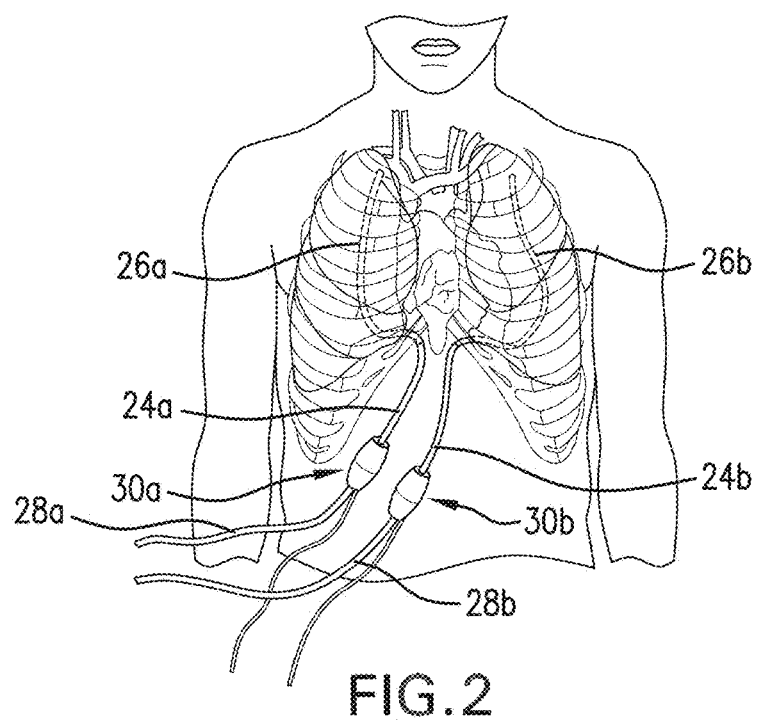
FIG. 2 is a schematic illustration of a patient's upper body with an embodiment of devices of the present invention coupled extrathoracically to chest tubes.

In the embodiment shown in FIG. 1, body 12 further comprises a fixation mechanism, such as clamp 22 connected to housing 13. Clamp can be integral with housing 13. Clamp 22 is configured to removably attach to catheter 14 in an operative state. A clamp is only one example of a suitable fixation member. Other fixation members can be used such as a clip, suction, clasp, sleeve, male-female fasteners, or any suitable combination thereof. In certain embodiments, the body of a device is integrally attached to the catheter providing an integrated system comprising a device and catheter as described in more detail below. FIG. 2 is a schematic illustration of an embodiment of a device 30 of the present invention and accompanying components inserted in a patient's body. Catheter 24 has an interior portion 26 inside the patient's body and an exterior portion 28 outside of the patient's body. In a preferred embodiment and as depicted in FIG. 2, device 30 is attached to the exterior portion 28 of the catheter 24.

Figure 3:
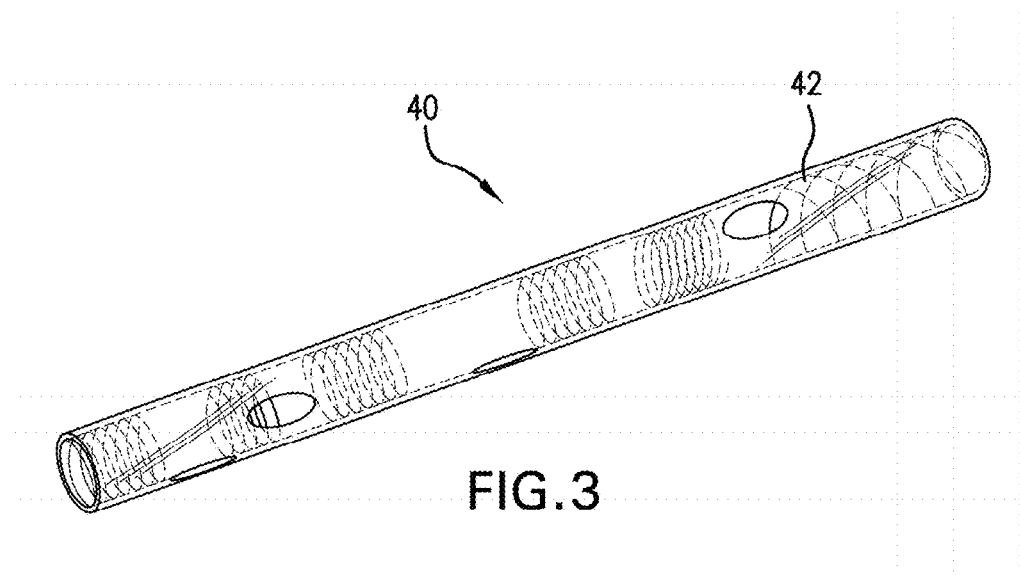
FIG. 3 is a perspective view of an embodiment of an integrated catheter, in particular a chest tube tip, according to the present invention. The walls of the catheter are enhanced with metallic components (several rods wrapped within the chest tube wall).

In embodiments, the present invention provides an integrated system comprising a device integrally connected to a catheter, such as a chest tube. The catheter can have the diameter of a standard chest tube (32-40 Fr), or a smaller diameter than standard chest tubes. In certain embodiments, the catheter has a diameter of about 20 Fr. The inner and outer surface of the catheter can be fabricated from a soft polymer, such as polyvinyl chloride. The walls of the tube can be enhanced with metallic components. Referring to FIG. 3, in an embodiment, several rods 42 are helically wrapped or braided within the chest-tube or catheter 40 wall. The number of rods and the helical pitch can be chosen to balance the goal of improved vibration transmission while avoiding stiffening the tube to the point where it is difficult to insert and possibly uncomfortable for the future patient. In another embodiment, the catheter is a custom laser-cut metal tube that allows flexing but still sufficient axial stiffness and capacity for improved vibration transmission. Since the laser-cut tube is a monolithic component, it will facilitate fabrication and may provide better vibration transmission. The catheter can include additional metallic components embedded in the chest-tube wall at the distal end to attenuate the vibration at this location. The vibration source can be directly coupled to the metallic elements within the integrated chest tube. Such vibration sources include piezoelectric actuators and solenoid mechanisms. In certain embodiments, the present invention provides a kit with an integrated system that includes different sizes of catheters, such as different chest tube sizes.

The system can also include an integrated power source. Preferably, the integrated system including the device and catheter is a single disposable unit. By "disposable" is meant that the device is not intended to be used more than a select number of times, such as one time.

In any of the embodiments of systems and devices of the present invention, preferably the devices are water-resistant. Also, to minimize patient discomfort due to potential pain from vibration, the devices of the present invention can be covered with an extrathoracic device cover in which the device is internally suspended. Further preferably, embodiments of systems of the present invention are instrumented to obtain one or more of the following measurements: 1) motor speed or frequency; 2) motor current; 3) vibration amplitude at the interface of the clamp and the chest tube or some other useful position on the device; 4) vibration amplitude at the distal end of the chest tube; and 5) vibration frequency at the distal end of the chest tube.

The present invention also provides embodiments of methods of minimizing obstruction of a catheter, such as a chest tube. In an embodiment, a method of minimizing obstruction of a catheter comprises delivering vibratory force to the catheter along the lumen towards the distal end of the catheter. The vibratory force is sufficient to minimize obstruction of the catheter by a biological substance. The vibratory force can be applied to the catheter by a motor or other vibration source that delivers vibration to the catheter sufficient to minimize catheter obstruction. Preferably, the vibratory force prevents or minimizes adherence of a biological substance to the inner and/or outer wall of the catheter and also help maintain the catheter's patency.

In an exemplary method, chest tubes are inserted in a patient's chest. The device body is tightly coupled (no tube compression) with the chest tubes inserted into the chest, exteriorized through the anatomical layers and secured to skin in a standard fashion as shown in FIG. 2. To complete the setting, the distal end of the chest tube is connected to collection canister with a vacuum suction attached (approximately 10-20 mm Hg). When the device is turned ON, the motion is conveyed to the functional portion (segment with holes and openings) of the chest tube (towards the internal portion of the tube and the tip). In particular, the electrical energy source is turned on to activate the motor and the vibration effect is conveyed along the tube inside the body towards the distal end of the tube.

The device can be an external attachment unit that does not interact directly with the sterile environment inside the tube and does not compromise the standard clinical setting of chest-tube use. In addition, the device can prevent or minimize clot attachment from the tube's outer surface as well, which in turn improves drainage through the holes of the tube that are kept open. This vibrational motion and its unique swirling effect on fluid inside the cylindrical tube is enhances the functional characteristics of the chest tubes currently used in cardiothoracic practice. However, as stated above, the device can be used in other settings where catheter occlusion is a risk factor.

EXAMPLES

Example 1

In Vitro Study

Figure 4:
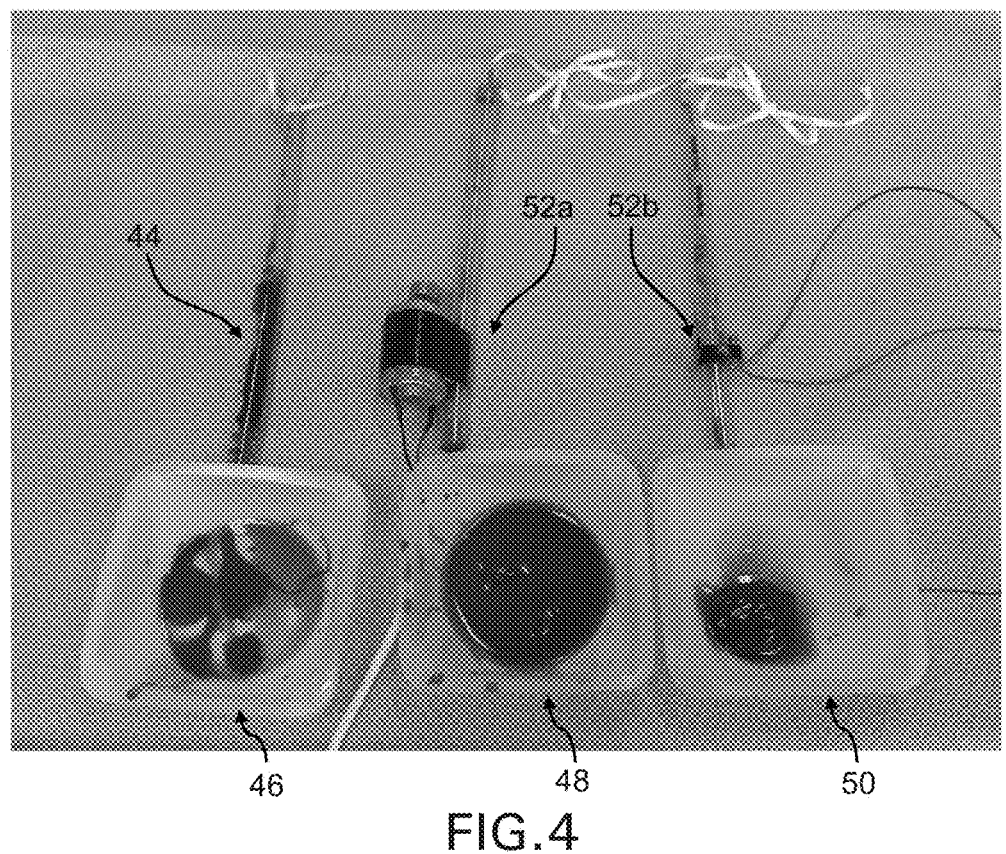
FIG. 4 is a photograph of the results of in vitro testing using an embodiment of a device of the present invention.

An in vitro test assessed the clotting inhibition of standard chest drainage tubes and tubes coupled with an embodiment of a device of the present invention. An embodiment of a device of the present invention included a DC motor (UC-28035-19160, Sinotech, Portland, Oreg.) with an eccentric mass (3.2 g, centroid radius of 4.53 mm) affixed to its motor shaft. Vibratory forces were varied by adjusting the current. COVIDIEN® 32 Fr chest tubes were used (Mansfield, Mass.), clamped at one end and filled with whole calf blood preserved with the anticoagulant mix of citrate-phosphate-dextrose-adenine. The test and control tubes were suspended vertically and blood was injected with human thrombin to induce clotting. The test tube was fitted with the embodiment of a device of the present invention and subjected to vibration; the control tube was not vibrated. After 10 minutes, the clamps were released and the movement of blood due to gravity was observed. Three trials were performed; the blood flowed freely from the test tubes 52a and 52b (with no residual adhesions to the chest tube wall but the control tube 44 was completely obstructed by clot as shown in FIG. 4. Further clots adhered to the tray 46 from which blood flowed from the control tube 44 but did not adhere to the trays 48 and 50 from which blood flowed from the test tubes 52a and 52b.

Example 2

In Vivo Study

Nine healthy pigs (Yorkshire mix, 46.0±3.3 kg) were used to evaluate the efficacy of the VibPate in an acute hemothorax model per the following protocol: All procedures were performed in a clean but non-sterile setting. The animals were placed on the surgical table in a supine position under general anesthesia, and two arterial lines were placed into the left and right carotid artery (for blood withdrawal).

A bilateral minithoracotomy was performed in the 6th intercostal space to insert blood infusion catheters and place Prolene sutures at the edge of the both lungs to create an injury after chest closure. A regular chest tube and a chest tube having an embodiment of a device of the present invention was inserted into the $7^{th}$ intercostal space bilaterally. The experiment started by causing mechanical lung injury, which triggered an intrinsic coagulation cascade (by pulling Prolene sutures), and then injecting blood into the chest. Hemodynamics, the amount of chest drainage, and device-related parameters such as vibration amplitude, frequency, and motor speed and current were monitored every 15 min for 2 hours. At the end of the experiment, the animal were euthanized with potassium chloride (3 mEq/kg) under a deep anesthesia (5% isoflurane), and a standard median sternotomy was performed to evaluate the residual blood and clots in the chest.

Figure 5:
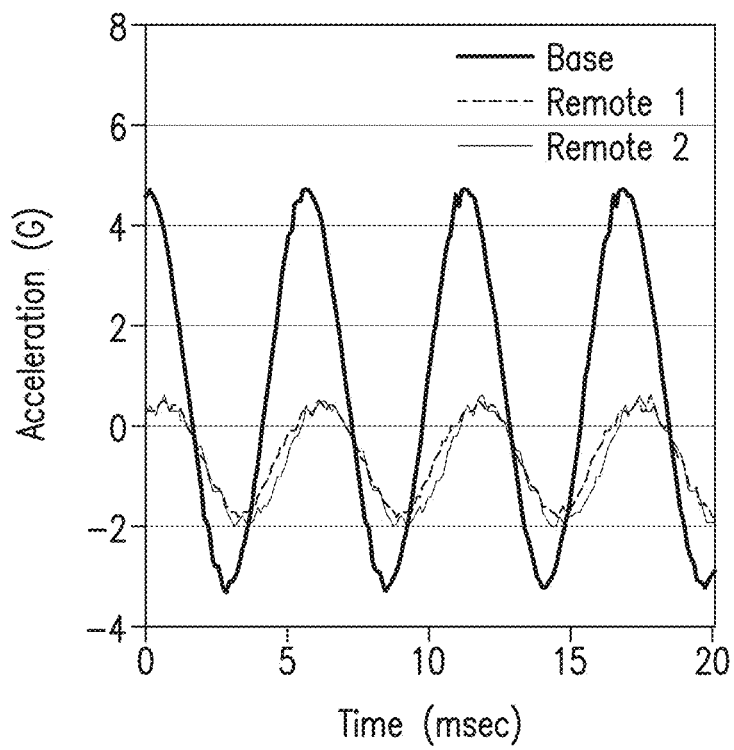
FIG. 5 is representative acceleration data in the animal experiments described in Example 2 below.
Figure 6:
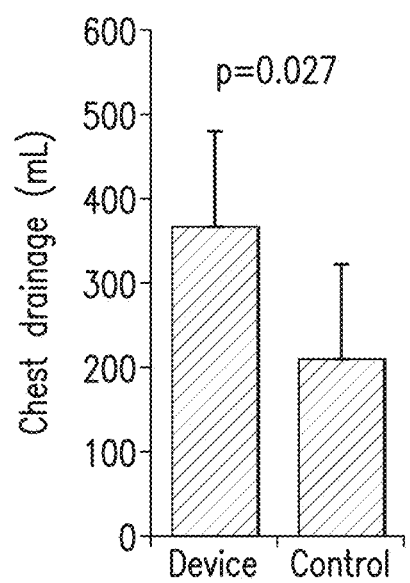
FIG. 6 is a graph depicting the blood drainage volume using 32 Fr chest tubes with an embodiment of a device of the present invention (VibPate) vs. 32 Fr standard tubes as control.

Referring to FIG. 5, acceleration data in 3 axes (x, y, and z) were measured with three accelerometers with the chest tube in place. A base accelerometer was placed on the embodiment of a device of the present invention that was placed on the extrathoracic portion of the chest tube. Two other accelerometers were remotely placed: Remote 1 was placed on the intrathoracic portion of the chest tube midway between the tip and the insertion site, and Remote 2 was placed at the distal end of the chest tube. In all 3 axes, there was some attenuation of acceleration at Remote 1 and Remote 2 compared with the base; however, vibration was successfully transmitted to the distal end of the chest tube. Total drainage volume was significantly (p=0.0274) higher when using the 32 Fr tubes fitted with an embodiment of a device (369±113 mL) vs. the 32 Fr standard chest tube used as Control (209±115 mL) as shown in FIG. 6. It is important to note that a more solid character of clots was observed with standard chest tubes. On the side of the chest tube with the embodiment of a device of the present invention, the clots were more fragile (easier to be broken). There were more visible luminal occlusions with standard tubes vs. minimal clot formation in the tubes attached to the embodiment of a device of the present invention. To compare the total volume of drainage and the amount of residual blood and clot in the chest, a Student's t test and a paired t test were used.

The embodiment of a device of the present invention had the ability to maintain chest-tube patency even when some amount of clot was attached to the tube connectors or partially attached to the tube wall. Throughout the study, the constant vibration maintained an uninterrupted drainage vs. only intermittent drainage observed in Control tubes. Thus, use of the embodiment of a device of the present invention showed significantly higher drainage volume and maintained chest-tube patency throughout the experiment. These results indicate that motion application to the chest tube wall may prevent postoperative clot deposition and subsequent build-up of a critical occlusion inside the tubes.

Example 3

General Animal Protocol

Figure 7:
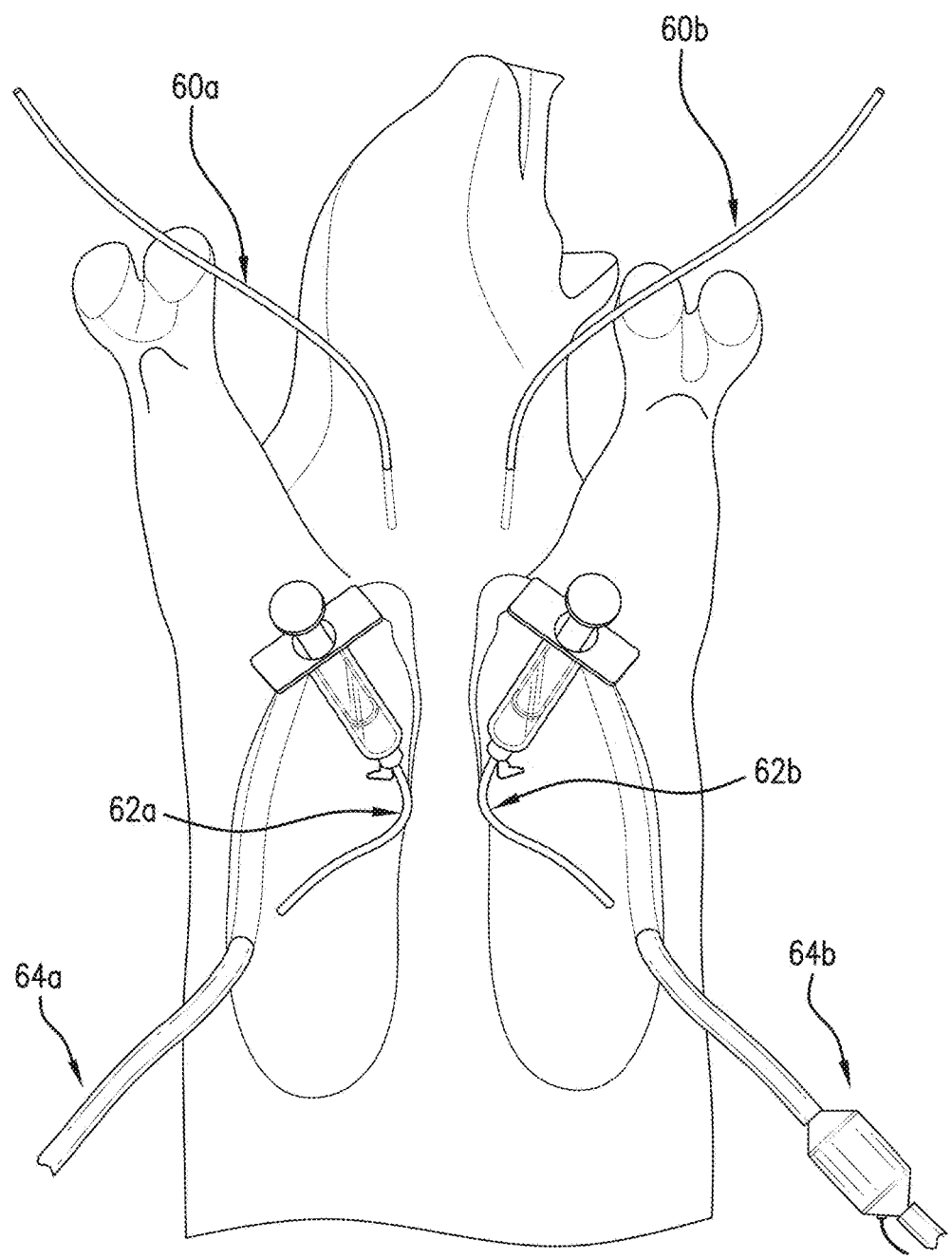
FIG. 7 is a schematic illustration of instrumentation used for an acute hemothorax model as described in Example 3 below.

A total of 26 male/female Yorkshire pigs (40-50 kg) are used for an acute hemothorax model as schematically illustrated in FIG. 7. Anesthesia is induced with an intramuscular injection of ketamine (20 mg/kg) and xylazine (5 mg/kg) and inhaled 5% isoflurane. The animals are placed supine on the operating table and, after placement of an endotracheal tube, the isoflurane concentration is reduced to 0.5%-2% for the duration of the experiment. All surgeries are performed under general anesthesia using isoflurane (0.5-2.5%).

Surgical Procedure

A right lateral neck incision is performed to isolate the right carotid artery and the jugular vein. The extrathoracic jugular vein is cannulated with an 8 Fr introducer sheath. The right carotid artery is exposed and cannulated with fluid-filled lines 60a and 60b. An arterial line is placed into the left carotid artery after performing a left lateral neck incision. A minithoracotomy is performed bilaterally in the 6th intercostal space. The inferior edge of the left and right lower lobe of the lung is grasped, and a 0-Prolene stitch is placed 2 cm from the edge. To initiate blood clotting by releasing of tissue factors from the wound, the Prolene sutures brought out of from the closed chest are pulled to cause a tear in the lung tissue. Two soft catheters (8 Fr) 62a and 62b are placed through the minithoracotomy sites and used subsequently for introduction of blood into the pleural space. The chest tubes 64a and 64b are inserted in the 7th intercostal space bilaterally (32 Fr standard tube 64a for one side and an embodiment of a device of the present invention on another chest tube 64b on the opposite side), with both tubes clamped; the site of the device is switched in each next experiment. The thoracotomy is closed in layers, and chest tubes are connected to drainage canisters at −20 cm H.sub.2O suction. The clamps on the chest tubes are released to allow drainage. At baseline (time zero), a lung injury is induced by pulling the Prolene sutures, and 120 mL of withdrawn arterial blood is injected into each pleural space through the previously placed 8 Fr sheath. Every 15 min thereafter, another 120 mL of blood is withdrawn from the arterial line and infused into each pleural cavity (a total of seven times) until a total of 840 mL of blood is introduced into each pleural cavity. The mean arterial pressure is maintained above 60 mm Hg. The blood drained from each thoracic cavity is recorded every 15 min for 2 hours. Blood gas analysis to monitor the oxygenation state and hemoglobin levels is obtained every 30 min.

At the end of the 2-hour period, the animal is euthanized. A median sternotomy is performed. All residual blood and clots are carefully evaluated for total volume. Photographs of the tubes are taken to assess the presence of internal thrombus and adjacent clots.

Based on data from preliminary studies, the average standard deviation of the total drainage of the control tubes was 115 mL. According to the following equations, n≥6 animals (per each set of in vivo studies using a clamped and integrated system embodiment, and in vivo tests with smaller tubes) detects a difference in the total drainage amount between the two chest tubes of 150 mL at an alpha level of 0.05 and a power of 80%.

$$n=2\times(\Phi\sigma/\Delta)^2$$

where n=sample size, Φ=parameter determined by the Gauss distribution of the endpoint variable (2.326 for an ideal statistical power reaching 80%), σ=expected standard deviation of the total drainage amount (115 mL), and Δ=difference of the total drainage amount between the two chest tubes.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A device comprising:
a body configured to attach to a medical device in an operative state, the medical device having a lumen or hollowed portion, the body comprising:
a housing including a motor configured to deliver mechanical motion to the medical device along the lumen or hollowed portion in a manner configured to induce a swirling motion in liquids being transported through the lumen, the swirling motion in the liquids being sufficient to prevent biological substances from adhering to the inner walls of the lumen or hollowed portion of the medical device and thereby minimize obstruction of the medical device's lumen or hollowed portion.

2. The device of claim 1, wherein the medical device is a catheter.

3. The device of claim 1, wherein the mechanical motion is vibration, fluctuation, oscillation, or any suitable combination thereof.

4. The device of claim 1, wherein the body is integrally attached to the medical device.

5. The device of claim 1, further comprising a fixation member integrally attached to the housing and sized and configured to receive the medical device, wherein the fixation member is configured to permit the housing to be connected to the medical device at a desired fixation position along the length of the medical device, the fixation member being configured to permit the fixation position to be adjusted.

6. The device of claim 5, wherein the fixation member is a clamp.

7. The device of claim 1, wherein the device is configured so that a motor shaft of the motor rotates about a motor axis parallel to the lumen or hollowed portion of the medical device.

8. The device of claim 7, further comprising an eccentric weight connected to the motor shaft, wherein the motor is operative to rotate the eccentric weight about the motor axis in order to apply the mechanical motion to the medical device.

9. A system comprising:
a medical device having a lumen or hollowed portion; and
a device comprising a body configured to couple to the medical device in an operative state, the body comprising a housing including a motor, the motor configured to deliver mechanical motion to the medical device along the lumen or the hollowed portion in a manner configured to induce a swirling motion in liquids being transported through the lumen, the swirling motion in the liquids being sufficient to prevent biological substances from adhering to the inner walls of the lumen or hollowed portion of the medical device and thereby minimize obstruction of the lumen or hollowed portion of the medical device.

10. The system of claim 9, wherein the medical device is a catheter.

11. The system of claim 9, further comprising a fixation member integrally attached to the housing and sized and configured to receive the medical device, wherein the fixation member is configured to permit the housing to be connected to the medical device at a desired fixation position along the length of the medical device, the fixation member being configured to permit the fixation position to be adjusted.

12. The system of claim 9, wherein the device is configured to couple to the medical device so that a motor shaft of the motor rotates about a motor axis parallel to the lumen or hollowed portion of the medical device.

13. The system of claim 12, further comprising an eccentric weight connected to the motor shaft, wherein the motor is operative to rotate the eccentric weight about the motor axis in order to apply the mechanical motion to the medical device.

14. A method of minimizing obstruction of a medical device having a lumen or hollowed portion comprising:
obtaining a device comprising a housing including a motor configured to deliver mechanical motion to the medical device along the lumen or the hollowed portion of the medical device;
attaching the device to the medical device; and
activating the device to deliver mechanical motion to the medical device and cause a swirling effect on fluid flowing through the lumen or hollowed portion of the medical device, the motion being sufficient to minimize obstruction of the lumen or hollowed portion of the medical device by a biological substance.

15. The method of claim 14, wherein the motion prevents, minimizes, or influences adherence of the biological substance to the inner and/or outer wall of the medical device.

16. The method of claim 14, wherein the motion helps maintain the medical device's patency.

17. The method of claim 14, wherein the motion helps maintain the medical device's flow characteristics.

18. The method of claim 14, wherein attaching the device to the medical device comprises coupling the device to the medical device so that a motor shaft of the motor rotates about a motor axis parallel to the lumen or hollowed portion of the medical device.

19. The method of claim 18, wherein the body further comprises an eccentric weight connected to the motor, wherein activating the device causes the motor to rotate the eccentric weight about the motor axis in order to apply the mechanical motion to the medical device.

* * * * *